(12) United States Patent
Roehner et al.

(10) Patent No.: US 6,841,779 B1
(45) Date of Patent: Jan. 11, 2005

(54) MEASUREMENT OF WAX PRECIPITATION TEMPERATURE AND PRECIPITATED SOLID WEIGHT PERCENT VERSUS TEMPERATURE BY INFRARED SPECTROSCOPY

(75) Inventors: Richard Roehner, Sandy, UT (US); Francis V. Henson, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 122 days.

(21) Appl. No.: 10/225,917

(22) Filed: Aug. 22, 2002

Related U.S. Application Data

(60) Provisional application No. 60/314,871, filed on Aug. 24, 2001.

(51) Int. Cl.[7] ............................................. G01N 33/26
(52) U.S. Cl. .............................. 250/339.07; 250/339.06
(58) Field of Search ....................... 250/339.07, 339.06, 250/338.1, 336.1

(56) References Cited

U.S. PATENT DOCUMENTS

| | | | | |
|---|---|---|---|---|
| 5,891,262 A | * | 4/1999 | Khalil et al. | ............ 134/22.11 |
| 6,035,706 A | * | 3/2000 | Campagnolo et al. | ..... 73/64.42 |
| 2003/0075478 A1 | * | 4/2003 | Beasley et al. | ............... 208/33 |

FOREIGN PATENT DOCUMENTS

| GB | 2300272 A | * 10/1996 | ......... G01N/33/28 |
|---|---|---|---|

OTHER PUBLICATIONS

Zerbi, G.; Gussoni, M.; Magni, R.; Mortiz, K.H.; Bigotto, A.; Dirlikov, S. Molecular Mechanics for Phase Transition and Melting of n–Alkanes: A Spectroscopic Study of Molecular Mobility of Solid n–Nonadecane. *J. Chem. Phys.* 1981, 75, 3175–3194.

Snyder, R. G.; Maroncelli, M.; Qi, S.P.; Strauss, H.L. Nonplanar Conformers and the Phrase Behavior of Solid n–Alkanes, *J. Am. Chem. Soc.* 1982, 104, 6237–6247.

Smith, B. *Infrared Spectral Interpretation, A Systematic Approach*. CRC Press: New York, 1999, p. 36.

Snyder, R.; Maroncelli, M.; Strauss, H. L; Hallmark, V. Temperature and Phase Behavior of Infrared Intensities: The Poly(methylene) Chain. *J. Phys. Chem.* 1986, 90, 5623–5630.

Snyder, R. G.; Goh, M. C.; Srivatsavoy, V.; Strauss, H.; Dorset, D. L. Measurement of the Growth Kinetics of Microdomains in Binary n–Alkane Solid Solutions by Infrared Spectroscopy. *J. Phys. Chem.* 1992, 96, 10008–10019.

Smith, C.; Schuetz, C.; Hodgson, R. Relationship Between Chemical Structures and Weatherability of Coating Asphalts as Shown by Infrared Absorbtion Spectroscopy. *Ind. Eng. Chem. Prod. Res. Dev.* 1966, 5, 153–161.

Gupta, A. K.; Brouwer, L.; Severin, D. Phase Transitions in Petroleum Waxes Determined by Infrared Sectroscopy. *Petrol. Sci. Technol.* 1998, 16, 59–69.

Alex, R. F.; Fuhr, B. J.; Klein, L. L. Determination of Cloud Point for Waxy Crudes Using a Near–Infrared / Fiber Optic Technique. *Energy Fuels* 1991, 5, 866–868.

* cited by examiner

*Primary Examiner*—David Porta
*Assistant Examiner*—Christine Sung
(74) *Attorney, Agent, or Firm*—Thorpe North & Western, LLP

(57) ABSTRACT

Disclosed is a FT-IR spectroscopy method for the determination of the wax precipitation temperature, and the estimation of the amount of precipitated solid wax material (both crystalline and amorphous) present in a liquid hydrocarbon, such as a petroleum crude oil.

8 Claims, 13 Drawing Sheets

MEASUREMENT OF WAX PRECIPITATION TEMPERATURE AND PRECIPITATED SOLID WEIGHT PERCENT VERSUS TEMPERATURE BY INFRARED SPECTROSCOPY

RELATED APPLICATIONS

This application claims priority from U.S. Provisional Patent Application No. 60/314,871, filed 24 Aug. 2001.

STATEMENT REGARDING FEDERALLY SPONSORED RESEARCH OR DEVELOPMENT (Not applicable)

FIELD OF THE INVENTION

This invention relates to methods for the determination of wax precipitation temperature.

BACKGROUND OF THE INVENTION

Many crude oils can be described as paraffinic-intermediate type, which precipitate solids with reduction in temperature. Among these oils are the crude oils currently produced, for example, on the North Slope of Alaska, certain crude oils produced in the Gulf of Mexico, and crude oils produced in the Grand County, Utah. The oils from the North Slope of Alaska are currently commingled and blended with gas condensate (resulting from the processing of liberated reservoir solution gas) for transport in the 800-mile, 48-inch diameter, Trans-Alaska Pipeline System (TAPS). The commingled blend is referred to herein as Alaska North Slope (ANS) crude oil.

Heat losses from the warmer crude oil to the environment during transport in the pipeline can result in the reduction of the crude oil temperature, and subsequent formation of a solid phase in the crude oil. The original design of TAPS was based on properties for crude oil from the Prudhoe Bay oil field, blended with gas condensate liquids. This design, for 2 MMBPD maximum pipeline throughput, allowed for short term pipeline operation with high crude oil precipitated solids content during start-up, and for restart of the pipeline after a potential prolonged shutdown during cold mid-winter conditions. The flow of crude oil through TAPS peaked in 1988 at 2 MMBPD and is estimated to be 1.04 MMBPD in 2000. Future crude oil transported in TAPS is expected be a more diverse blend of crude oils from North Slope oil production operations. Other liquids proposed for transport in TAPS include heavy oil, offshore light crude and condensate fields, and Fischer-Tropsch gas-to-liquid (GTL) conversion products. This potential combination of low pipeline flowrates and differing oil types raises questions regarding the amount of wax precipitation which may occur in future TAPS operating modes.

Operating problems relating to the formation of a solid phase in the crude oil transported in TAPS include the following: inability to properly measure standard volumes, increased solids deposition in pipeline and storage tanks, increased liquid viscosity and pumping costs, and the inability to restart the pipeline after a prolonged shutdown in cold conditions due to the yield strength developed by gelled crude oil. It is important to identify the variables, which determine the amount of solids precipitated during crude oil transport as a first step in minimizing detrimental transport effects. These variables are known to include temperature, pressure, composition, and flow rate. Temperature affects liquid-solid equilibria, while pressure effects are minimal due to the low values of Poynting factors for crude oil components. The composition of the crude oil is a primary variable both in terms of light ends (carbon number less than 7) composition of the crude, and the actual content of solid forming components present in the heavy ends (carbon number greater than 25) of the crude oil. Flow rate is believed to affect solid-liquid equilibria by shear-induced modification of wax crystal and micellar-colloidal structures, and the generation of streaming potentials from the flow of charged colloidal particles.

The amount of solid material suspended in crude oil at any given temperature affects the potential for solid deposition. Thus, the ability to predict the appearance temperature and the amount of a solid phase in a crude oil are both essential for the prediction of the amount of solid deposited. This information is also necessary for the selection of solid management practices. The need for a model capable of predicting liquid-solid equilibria for current and future crude oils of a paraffinic-intermediate type character that precipitate solids at reduction of temperature has been identified as an important issue related to the transport of reserves of these oils.

There are analytical methods for the measurement of wax precipitation temperature (WPT), weight percent solid versus temperature, and phase transition thermodynamic properties (i.e., latent heat of fusion). There are also methods that are related and are those used to compare solid deposition by crude oils, and methods which provide qualitative indication of the stability of crude oils with regard to precipitation of solids from crude oil, are also of related interest.

Since the determination of WPT and the amount of solid wax precipitated below WPT are critical for understanding crude oil rheology and solids deposition, there have been many methods proposed for the determination of WPT. These include viscometry, cross polarized microscopy (CPM), differential calorimetry (DSC), densitometry, near-IR spectroscopy (NIR), and acoustic resonance technology (ART). Filtration and centrifugation have been used for determining solid wax content versus temperature for crude oil systems, even through the results are questionable because of occluded oil and there are difficulties for high pressure applications. Pulsed $^1$H NMR and DSC have also been used, but are problematic and ineffective for low wax crude oils, and crude oils that produce solids of low crystallinity. Infrared spectroscopy has been used to identify solid-solid and solid-liquid phase transitions for alkanes and petroleum waxes, and as an indicator of methylene crystallinity in petroleum derived asphalts.

Infrared spectroscopy methods, such as Fourier transform-infrared (FT-IR) spectroscopy, have been used in crude oil analysis to provide details about specific molecular structures, and characterize precipitated solids. For example, FT-IR has been used to determine the presence of long chain methylene carbons in asphalt materials[1]. Identification has been made by use of an infrared absorbtion doublet at 720 cm.[1,2] FT-IR has also been used to measure solid-solid, and solid-liquid transition temperatures of certain waxes by measuring the change in intensity with temperature of the 720 cm$^{-1}$ absorbtion band corresponding to methylene chain rocking.[3]. This is possible because the 720 cm$^{-1}$ band is specific to the $CH_2$ rocking vibration[7]. As disclosed in Snyder et al.[8] the infrared band intensities of the 735–715 cm$^{-1}$ $CH_2$ rocking mode bands of crystalline pure n-alkanes and PE increase with decreasing temperature at a magnitude much larger than predicted from temperature associated changes in density and refractive index.

A near-IR/fiber optics method has also been used to measure the WPT and asphaltene appearance point (AAP) of waxy crude oils. By monitoring the absorbance at 1450 nm wavelength (6896 cm$^{-1}$ wave number) of a sample of waxy South China Sea crude oil, the WPT of the sample could be determined from a break point in the absorbance curve produced.[4] The absorbance of the sample was measured in-situ using a fiber optic probe inserted into a mixed PVT cell apparatus.

Mid-infrared spectroscopy has been used to identify solid-solid and solid-liquid phase transitions for alkanes[5,6] and petroleum waxes,[3] and as an indicator of methylene crystallinity in petroleum derived asphalts[2]. It is believed that FT-IR spectroscopy had never been applied to the investigation of wax precipitation.

Measurements of ANS crude oil WPT and weight percent solid versus temperature using conventional methods (i.e., CPM) have been problematic, and in some cases, unsuccessful (i.e., DSC, $^1$H NMR). For these reasons, there is a need for yet another method for analyzing WPT that can successfully measure WPT for oils like ANS crude oil.

Terms and Definitions

The term "crude oil" refers to petroleum hydrocarbons which have undergone production and processing steps to remove solution gases present in the parent reservoir oil (or "live oil") to the degree required for pipeline transport and storage in tankage at atmospheric pressure. The term "stock tank oil" (STO) is also used to describe this type of crude oil. ANS crude oil refers to commingled Alaska North Slope crude oil blend transported in the TAPS. The term "crude oil light ends" is defined to be $C_7^-$ components, and includes $CO_2$, methane, ethane, propane butanes, and pentanes. The term "heavy oil" is typically reserved for crude oils with an API gravity of less than 20. The term "crude oil solids" refers to organic solids, as opposed to inorganic solids. Inorganic solids are present in TAPS crude oil at ppm levels, and originate from reservoir sand (silicates) and corrosion. Crude oil solids may be comprised of waxes, asphaltenes, emulsions, degraded drag-reducing agent, and a myriad of solidified oil-field chemical additives used for corrosion protection, production stimulation, and emulsion breaking.

The general term "wax" refers to solid material comprised primarily of paraffin with single carbon numbers (SCN) ranging from $C_{15}$ to $C_{60}$. This material often includes entrapped or co-precipitated crude oil, asphaltene solids, and inorganic material. Wax can remain in suspension in crude oils, or deposit on wetted surfaces through a variety of mechanisms. Waxes have been classified in the historical literature of the refining industry by a variety of terms representing the source and nature of the wax such as slack wax, scale wax, tank wax, soft wax, hard wax, etc. The common classification terms "macrocrystalline wax" and "microcrystalline wax" are used to differentiate the extremes of the range of variation found in wax solids produced from crude oil. Macrocrystalline wax refers to wax primarily comprised of n-paraffins that form large needle-like crystals which are observable in a low power optical microscope using a cross-polarized light source.

Microcrystalline wax refers to wax containing large amounts of iso-paraffins, naphthenes, and branched aromatics, which form very small crystals and are difficult to observe with a low power optical microscope. Microcrystalline wax is sometimes referred to as amorphous wax, due to the lack of a defined crystal structure. In general, microcrystalline waxes have higher molecular weights, densities, and refractive indices than macrocrystalline waxes. Macrocrystalline waxes are more likely to produce major problems (i.e., blockage) in crude oil production and transportation operations. Most tank bottom sludges are microcrystalline waxes. The term wax is used herein to refer to all organic solids, because waxes have historically been the primary contributor to solid materials precipitated by TAPS crude oil.

The terms "wax precipitation temperature," "wax appearance temperature," and "cloud point" have been used interchangeably in the literature to indicate the temperature at which wax crystallization commences. Wax precipitation temperature (WPT) will be the term used herein. The value obtained for a WPT for the same crude oil is often method dependent and therefore any value reported for WPT should also include the measurement method. It is important to note that crude oil systems at temperatures above the WPT may still contain organic solids comprised of asphaltenes and resins.

The invention is applicable for measuring the properties of any suitable liquid hydrocarbon mixture where was precipitation temperature and percent solids is required. This includes not only crude oil, but any other mixture of hydrocarbons, naturally occurring petroleum samples, fractions from distillation, cracking or any other chemical process, heavy oils, light crudes and condensates, or Fischer-Tropsch gas-to-liquid (GTL) conversion products.

List of References

1. Snyder, R. G.; Goh, M. C.; Srivatsavoy, V.; Strauss, H.; Dorset, D. L. Measurement of the Growth Kinetics of Microdomains in Binary n-Alkane Solid Solutions by Infrared Spectroscopy. *J. Phys. Chem.* 1992, 96, 10008–10019.

2. Smith, C.; Schuetz, C.; Hodgson, R. Relationship Between Chemical Structures and Weatherability of Coating Asphalts as Shown by Infrared Absorbtion Spectroscopy. *Ind. Eng. Chem. Prod. Res. Dev.* 1966, 5, 153–161.

3. Gupta, A. K.; Brouwer, L.; Severin, D. Phase Transitions in Petroleum Waxes Determined by Infrared Sectroscopy. *Petrol. Sci. Technol.* 1998, 16, 59–69.

4. Alex, R. F.; Fuhr, B. J.; Klein, L. L. Determination of Cloud Point for Waxy Crudes Using a Near-infrared/Fiber Optic Technique. *Energy Fuels* 1991, 5, 866–868.

5. Zerbi, G.; Gussoni, M.; Magni, R.; Moritz, K. H.; Bigotto, A.; Dirlikov, S. Molecular Mechanics for Phase Transition and Melting of n-Alkanes: A Spectroscopic Study of Molecular Mobility of Solid n-Nonadecane. *J. Chem. Phys.* 1981, 75, 3175–3194.

6. Snyder, R. G.; Maroncelli, M.; Qi, S. P.; Strauss, H. L. Nonplanar Conformers and the Phase Behavior of Solid n-Alkanes. *J. Am. Chem. Soc.* 1982, 104, 6237–6247.

7. Smith, B. Infrared Spectral Interpretation, *A Systematic Approach*. CRC Press: New York, 1999, p 36.

8. Snyder, R.; Maroncelli, M.; Strauss, H. L.; Hallmark, V. Temperature and Phase Behavior of Infrared Intensities: The Poly(methylene) Chain. *J.Phys. Chem.* 1986, 90, 5623–5630.

BRIEF SUMMARY OF THE INVENTION

An aspect of the present invention is a method for determining the wax precipitation temperature and percent solids for a petroleum sample. The absorbance of the sample is measured using Fourier transform-infrared (FT-IR) spectroscopy at the band near 720 cm$^{-1}$ that corresponds to the $CH_2$ rocking vibration of long chain methylene (LCM). Several points are measured at different temperatures to obtain a plot of data points of total (integrated) absorbance ($A_{TOTAL}$) vs. temperature.

Because of the splitting of the absorbtion peak from out-of-phase rocking in the closely packed LCM carbons in the orthorhombic crystals. The measurement of the infra-red light absorbance is made not merely as a measurement of the peak magnitude, but a peak area is determined in the range to include the split peak, for example, between about 735 and 715 cm$^{-1}$. Thus, when reference is made to absorbance measured at 720 cm$^{-1}$, what is meant herein is an integrated total absorbance measurement of the peak area between about 736 and 715 cm$^{-1}$.

Referring to FIGS. 3, 11, 14 as examples, the plot is characterized by two essentially linear lines, one for data points above the WPT, and one for data points below the WPT. These lines intersect at a temperature that corresponds to the point where waxes begin to precipitate, i.e., the wax precipitation temperature (WPT). Thus, WPT can be calculated from the data points using suitable regression techniques by determining that temperature at which the slope of total absorbance vs. temperature changes. This change can be determined by visual observation of a graph of the data, by suitable automated computer techniques, any suitable mathematical regression system, or any other suitable method. A suitable method of determining the point of change of slope is to generate the equations for the two lines by regression analysis and extrapolate the two linear lines to a point of intersection.

The weight percent (wt. % S) of solids at each temperature below the WPT can then be determined by the $A_{TOTAL}$ at any temperature point using the formula;

$$\text{wt \%} = [(A_{TOTAL} - A_L)/A_{TOTAL}] \times 100 \quad (1)$$

$A_L$ is the liquid absorbance at the selected temperature and is determined by extrapolating the data of total absorbance vs. temperature from the data points above the WPT to the selected temperature below the WPT. Referring again to FIG. 3, the circles represent such extrapolated points ($A_L$). Thus, the solid content fraction at a particular temperature is determined by subtracting the value of the circle data point ($A_L$) from the corresponding square data point ($A_{TOTAL}$) and dividing by $A_{TOTAL}$.

The invention is applicable for measuring the properties of any suitable liquid hydrocarbon mixture where was precipitation temperature and percent solids is required. This includes not only crude oil, but any other mixture of hydrocarbons, naturally occurring petroleum samples, fractions from distillation, cracking or any other chemical process, heavy oils, light crudes and condensates, or Fischer-Tropsch gas-to-liquid (GTL) conversion products.

DETAILED DESCRIPTION OF THE INVENTION

Figure 1:
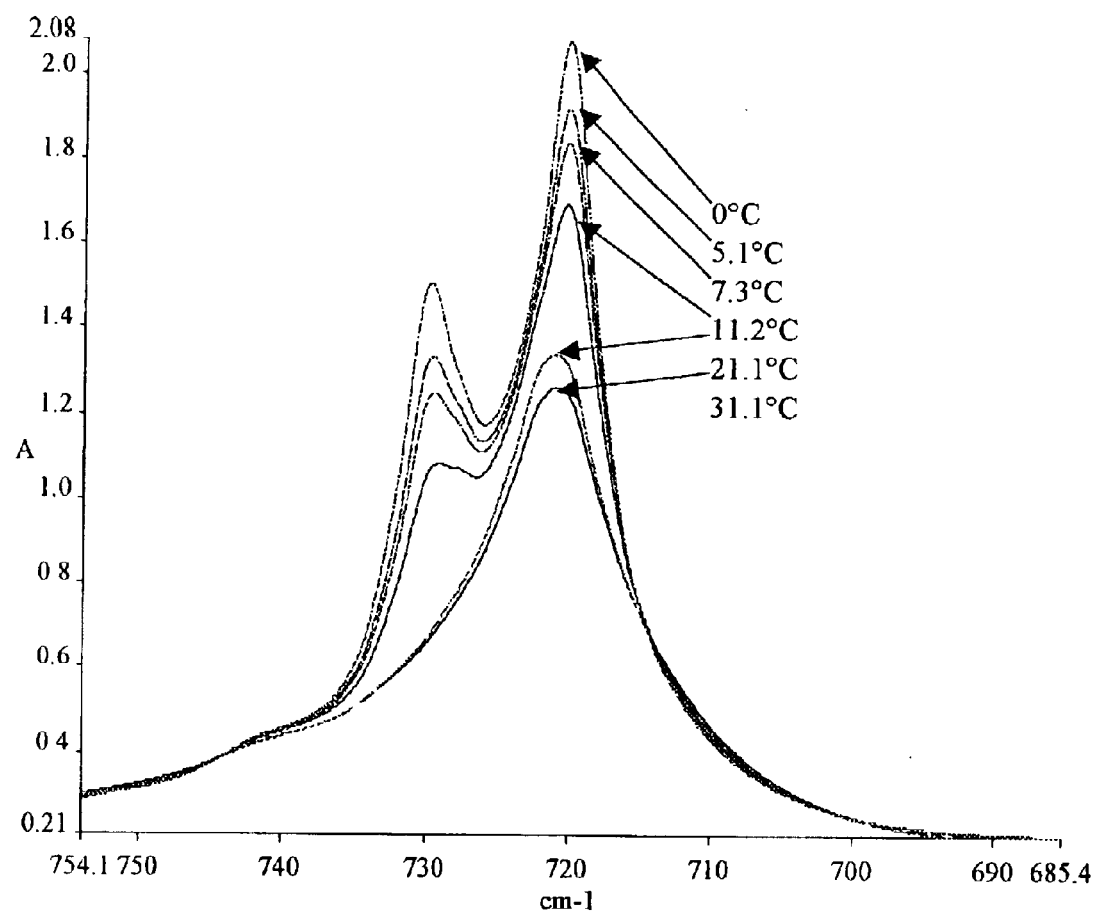
FIG. 1 is a graph of spectra of Model Oil, Aliquot B at 720 cm$^{-1}$.

Measurement of WPT, and Estimation of Weight Percent Solid Versus Temperature by FT-IR Spectroscopy Background FT-IR spectroscopy measures the absorbance associated with molecular vibrations present in the sample analyzed. The Beer-Lambert Law defines absorbance (A) as:

$$A = abc \quad (2)$$

where a is the absorptivity, b is the sample path length, and c is the concentration of the component providing the absorbance. Noting that for multicomponent systems absorbance at a given wavenumber is additive the absorbance can be expressed as, $$A_v = \Sigma(a_i b c_i) \quad (3)$$

where the subscript i denotes components of differing absorptivity, and the subscript v denotes the specific wavenumber. The band at approximately 720 cm$^{-1}$ has been associated with the existence of long chain methylene (LCM) carbon for hydrocarbon systems. The LCM carbon is defined as having more than four CH$_2$ groups in a row. The 720 cm$^{-1}$ band is specific to the —CH$_2$— rocking vibration. As the temperature of a sample containing large amounts of LCM carbon is decreased below the WPT, the peak grows in intensity due to density change with temperature, and due to the creation of the solid phase. Additional cooling of the sample containing LCM carbon below a solid-solid phase transition temperature (i.e. hexagonal to orthorhombic crystal), can result in splitting of the peak at 720 cm$^{-1}$ into a doublet. This splitting occurs due to out-of-phase rocking in the closely packed LCM carbons in the orthorhombic crystals. It should be noted that there is a threshold concentration required for the doublet to form. Monitoring these changes in the FT-IR spectra of crude oils provides important information describing liquid-solid equilibria since LCM carbon is the primary functional group contributing to solid wax formation in crude oils.

WPT Measurement

Equation 3 can be written in specific terms for the contribution due to the rocking of solid and liquid LCM carbons at 720 cm$^{-1}$ as shown in equation 4.

$$A_{720} = (a_l b c_l) + (a_s b c_s) \quad (4)$$

In equation 4, $a_l$ is the absorptivity of the liquid LCM carbon, $a_s$ is the absorptivity of the solid LCM carbon, $c_1$ is the concentration of the liquid LCM carbon, and $c_s$ is the concentration of the solid LCM carbon. Equation 4 can be rewritten as follows for the total measured absorbance at 720 cm$^{-1}$ $$A_{720} = A_{total} = A_l + A_s \quad (5)$$

The subscripts l and s denote liquid and solid absorbances, respectively. Assuming constant absorptivity of the LCM carbon in the liquid phase, the initial change in intensity at 720 cm$^{-1}$ is interpreted as a change in the total LCM carbon concentration due to the change in sample density with temperature. As the sample was cooled below the WPT, the creation of a solid phase comprised primarily of LCM carbon provides a distinct change in slope for a plot of $A_{total}$ measured at 720 cm$^{-1}$ versus temperature. This slope change in absorbance is due to the formation of the solid phase with a higher absorptivity. The temperature corresponding to the change in slope indicates the WPT.

Estimation of Weight Percent Solid Versus Temperature

The amount of solid LCM carbon present corresponds to the amount of solid present in the crude oil, since the solid usually consists of alkanes with a carbon number in excess of 25. The following equation was used to estimate the weight percent solids for crude oil systems:

$$\text{wt \% } S = [(c_s/c_{total})(f_{LCM\ carbon})(f_{carbon})(M)] \times 100\% \quad (6)$$

where $c_s$ is the concentration of LCM carbon in the solid phase, $c_{total}$ is the total concentration of LCM carbon in the solid and liquid phases, $f_{LCM\ carbon}$ is the fraction of the carbon in the sample that is LCM, $f_{carbon}$ is the fraction of the total sample comprised of carbon, and M is a multiplier to account for the presence of material in addition to LCM carbon in the solid phase (i.e., asphaltenes, methyl carbon). Combining equations 4 and 5 for $c_s$ yields equation 7.

$$c_s = (A_{total} - A_l)/(a_s b) \quad (7)$$

If equations 6 and 7 are combined, an equation is obtained by which the weight percent solid can be estimated from the total absorbance at 720 cm$^{-1}$.

$$\text{wt \% } S = \{[(A_{total} - A_l)/(a_s b c_{total})](f_{LCM\ carbon})(f_{carbon})(M)\} \times 100\% \quad (8)$$

This equation could be used directly through determination of $f_{LCM\ carbon}$ by $^{13}$C NMR, $f_{carbon}$ by elemental analysis, and $a_s$ from FT-IR of the solid phase. However, it is possible to further simplify the equation to allow an estimation of the weight percent solid wax present below the WPT using only FT-IR measurements. To do this, we first note that the average sample absorptivity, $a_{av}$, for LCM carbon is a fraction, f, of the solid LCM carbon absorptivity.

$$a_{av} = f a_s \quad (9)$$

Replacing the solid absorptivity in equation 7 by the average absorptivity, and noting that, $$A_{total} = a_{av} b c_{total} \quad (10)$$

leads to equation 11.

$$\text{wt \% } S = \{[(A_{total} - A_l)/(A_{total})](f_{LCM\ carbon})(f_{carbon})(M)\} \times 100\% \quad (11)$$

If the fractional and multiplier factors are assumed to be independent of temperature, then we obtain equation 12, $$\text{wt \% } S = C[(A_{total} - A_l)/A_{total}] \times 100\% \quad (12)$$

where the constant C is $(f_{LCM\ carbon})(f_{carbon})/(M)$. Thus the solid wax content can be estimated from the total measured absorbance at 720 cm$^{-1}$ and the absorbance due to LCM carbon in the liquid state. Finally, it is assumed that the absorbance due to LCM carbon in the liquid state at temperatures below the WPT can be estimated by extrapolation of the absorbance versus temperature line obtained above the WPT.

Experimental Apparatus and Procedures

Overview

The experimental work included the determination of ANS crude oil and ANS crude oil solids compositions, the determination of wax precipitation temperatures, and the estimation of the amount of solid wax precipitated at TAPS operating temperatures. Several experimental techniques were used for key measurements to provide a comparative review of the methods.

Experimental Procedure

FT-IR Instrumentation

The FT-IR analysis was conducted using a Perkin Elmer 16PC Spectrometer, with Perkin Elmer Spectrum v2.0 software. Spectra were collected from 4000 cm$^{-1}$ to 650 cm$^{-1}$. The spectra were the average of 16 scans, with a spectral resolution of 4.0 cm$^{-1}$. A modified SpectraTech HC-32 liquid cell holder was used to control sample temperature. The sample temperature was measured with a calibrated Type-K thermocouple and an Omega HH-22 Digital Thermometer (±1.0° C.), and controlled (±0.1° C.) using a Brookfield HT-105 controller with a Brookfield TC-500 bath. NaCl windows (32 mm), with a 0.1 mm lead spacer, were used in the cell holder.

The HC-32 liquid cell holder thermocouple was always within 0.1° C. of the sample temperature for the cooling rates employed (0.05–0.20° C. per minute) and the experimental temperature range (−5.0–95° C.) used. The comparison was generated by placing a micro-thermocouple in the liquid cell, and comparing the micro-thermocouple temperature readings with the HC-32 liquid cell thermocouple readings on the digital thermometer for coolant temperature settings covering the anticipated operating range of experiments. Since the observed differences in temperature readings were less than the accuracy attributed to the thermocouples (±1.0° C.), the HC-32 liquid cell thermocouple temperature was used to represent the sample temperature.

Calculations

Total absorbance attributed to LCM rocking was represented by integrating the spectra between 735 cm$^{-1}$ and 715 cm$^{-1}$. This was based on the observed peak areas for n-alkanes ranging from $C_{22}$ to $C_{50}$, the desire to decrease data scatter, and the need to minimize the additive effects of any absorbance due to alkyl benzene compounds in crude oils (attributed to bands at approximately 740 cm$^{-1}$).

Integration was performed using the Spectrum 2.0 software Peak Area/Height routine. The corrected peak area obtained for each temperature was added to the base of the peak determined from the first temperature tested to obtain total absorbance at each test temperature. The base of the peak analyzed at the first test temperature was obtained by subtracting the corrected peak area obtained from the area/height routine, from the uncorrected peak area obtained from the area/height routine. This was done to eliminate the effect of baseline shifts, which might occur as the sample temperature was reduced.

The WPT determination for both a Model Oil (selected for known solid-liquid equilibria) and the ANS crude oil was accomplished by fitting linear relations to peak area data from both the start and end of the temperature range evaluated. Intersection of the two best-fit lines was taken to be the WPT, which was easily identified graphically within the accuracy of temperature measurement employed (±1.0° C).

Equation 12 was used to calculate an estimated weight percent solid for temperatures below the observed WPT, using the integrated peak areas for the absorbance values $A_{total}$, and $A_l$. Values for the liquid LCM carbon absorbance below the WPT were calculated using an equation for the peak area as a function of temperature, obtained by a linear regression fit to experimental peak area data obtained above the WPT. A value of C=1.0 was assumed for simplicity. This simplification was shown to produce reasonable approximations for precipitated wax contents of the systems investigated.

A more detailed description of the calculations used, along with a worked example for the analysis of an aliquot of the Model Oil, is shown below:

FT-IR CALCULATIONS

FT-IR Calculations—Model Oil, Aliquot A

Figure 2:
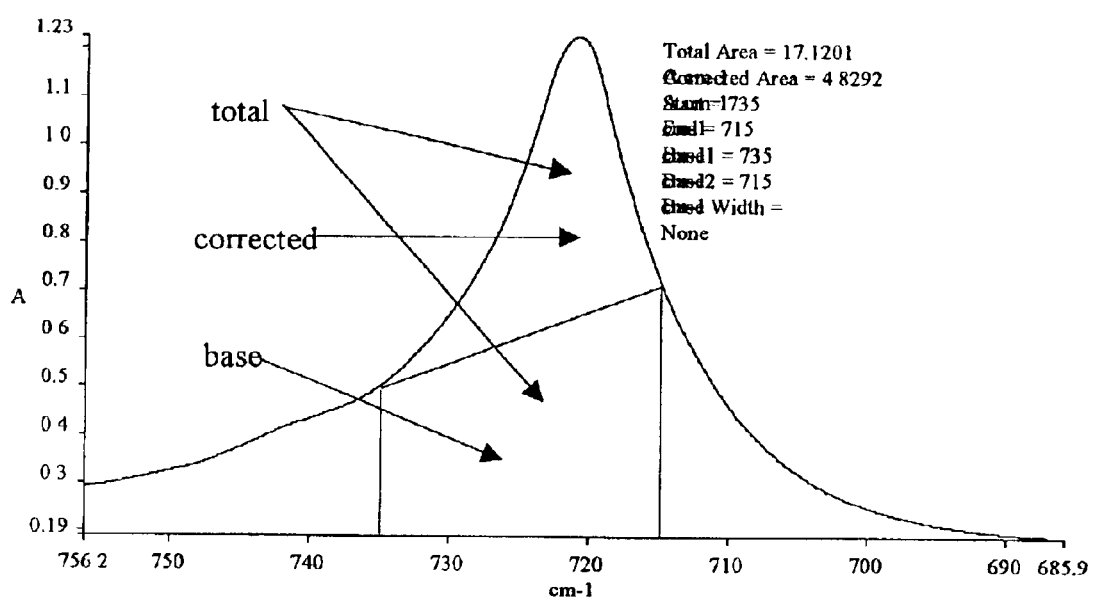
FIG. 2 is a graph illustrating FT-IR peak area calculations of Model Oil A at 35.4°
Figure 3:
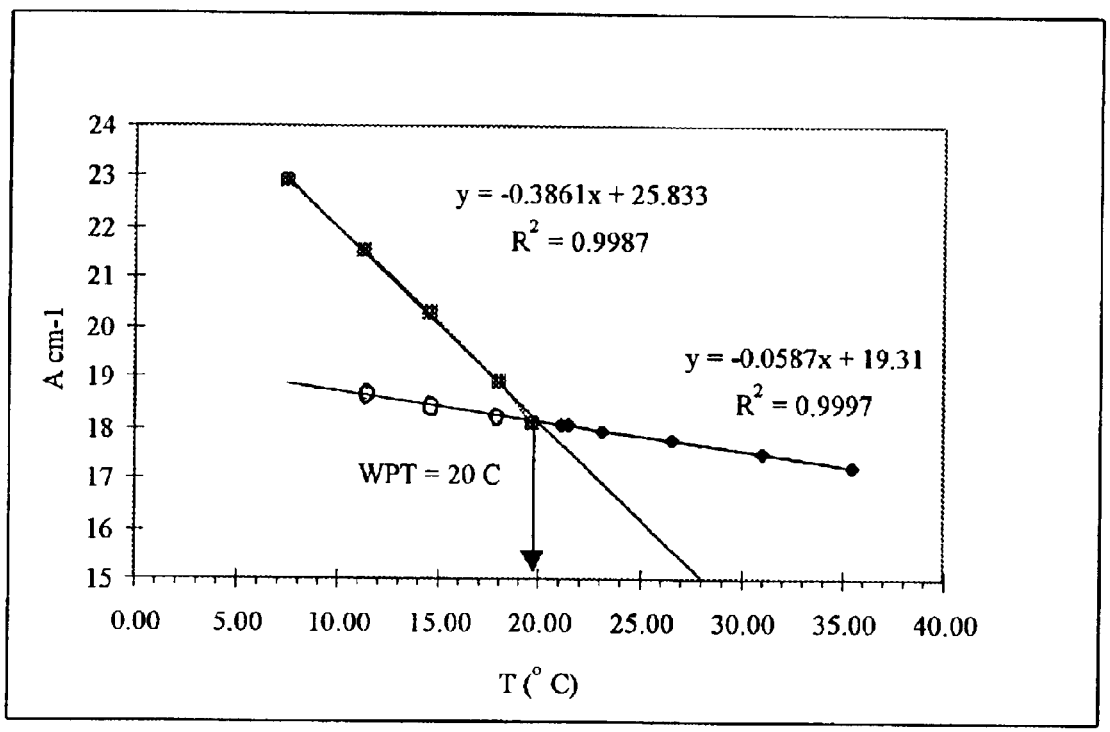
FIG. 3 is a graph of Peak Area (735–715 cm$^{-1}$) versus Temperature of Model Oil, Aliquot B.

The following example calculations are for determination of WPT and weight percent solid versus temperature of a sample of the Model Oil. The spectra obtained from FT-IR analysis are presented in FIG. 1. Peak area calculations are summarized in Table A. The spectra at each temperature are integrated to obtain the required area values from 735 cm$^{-1}$ to 715 cm$^{-1}$ using the Spectrum v2.0 software Peak Area/Height routine, as indicated in FIG. 2. The adjusted total peak area from Table A is plotted as a function of temperature in FIG. 3. This plot permitted graphical identification (±1° C.) of the WPT. Calculations for weight percent solid versus temperature are summarized in Table B. A visual representation of the calculation for weight percent solid is provided in FIG. 4 for a temperature of 5.1° C.

TABLE A

Model Oil, Aliquot A, FT-IR Peak Area Calculations.

| | Peak Area, 735–715 cm$^{-1}$, (A.cm$^{-1}$) | | | |
|---|---|---|---|---|
| T (° C.) | total[a] | corrected[b] | base[c] | adjusted total[d] |
| 35.4 | 17.1201 | 4.8282 | 12.2909 | 17.1201 |
| 31.0 | | 5.0768 | | 17.3677 |
| 26.5 | | 5.3059 | | 17.5968 |
| 23.1 | | 5.5091 | | 17.8000 |
| 21.4 | | 5.6194 | | 17.9103 |
| 19.9 | | 5.7083 | | 17.9992 |
| 18.0 | | 6.1568 | | 18.4477 |
| 14.5 | | 7.3271 | | 19.6180 |
| 7.3 | | 9.5836 | | 21.8745 |
| 5.1 | | 10.2987 | | 22.5896 |
| 0.3 | | 11.1941 | | 23.4850 |
| 0.0 | | 11.2458 | | 23.5367 |

[a]Total area from Spectrum v2.0 Peak Area/Height integration.
[b]Corrected area from Spectrum v2.0 Peak Area/Height integration.
[c]Base area from total area minus corrected area for first spectra.
[d]Adjusted total area is base area plus corrected area for all spectra.

TABLE B

Model Oil, Aliquot A, FT-IR Weight Percent Solid versus Temperature Calculations.

| | Absorbance - Peak Area 735–715 cm$^{-1}$ (A.cm$^{-1}$) | | |
|---|---|---|---|
| T (° C.) | adjusted total[a] | extrapolated liquid phase[b] | wt % solid[c] |
| 35.4 | 17.1201 | | |
| 31.0 | 17.3677 | | |
| 26.5 | 17.5968 | | |
| 23.1 | 17.8000 | | |
| 21.4 | 17.9103 | | |
| 19.9 | 17.9992 | | |
| 18.0 | 18.4477 | 18.0876 | 1.95 |
| 14.5 | 19.6180 | 18.2829 | 6.81 |
| 7.3 | 21.8745 | 18.6847 | 14.58 |
| 5.1 | 22.5896 | 18.8074 | 16.74 |
| 0.3 | 23.4850 | 19.0753 | 18.78 |
| 0.0 | 23.5367 | 19.0920 | 18.88 |

Figure 4:
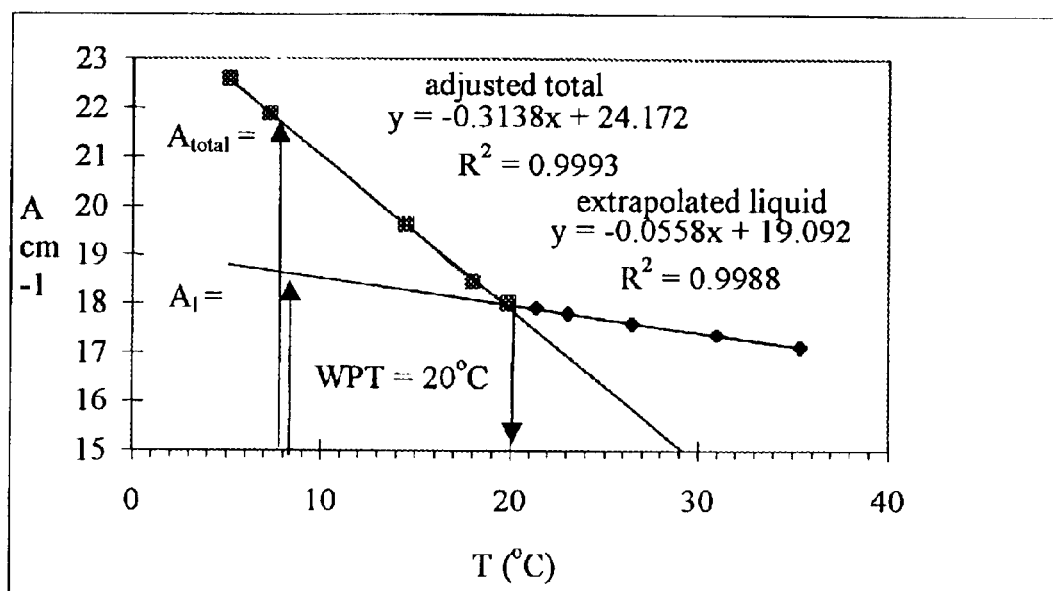
FIG. 4 is a graph showing Peak Area (735–715 cm$^{-1}$) versus Temperature for Model Oil, Aliquot A.

[a]Adjusted total absorbance - peak area from Table A.
[b]Extrapolated liquid phase absorbance peak area from regression equation.
developed as shown in FIG. 4.
[c]Weight percent solid calculated from equation 12,
wt % S = C [(A$_{total}$ − A$_1$)/A$_{total}$] × 100%,
where, C = 1.0

Model Oil Analysis

A Model Oil was analyzed using the FT-IR method to demonstrate the capability of the invention and compare the results with other methods analyzing the Model Oil. The Model Oil comprised of n-alkanes was purchased from Supelco as a custom mix.

The composition of the Model Oil is reported in Table C. Chemicals used to make the mix were of 98 to 99% purity. Prior to sampling the mixture, the sample was heated to 40° C. (approximately 20° C. above the WPT) for 1 hour. Aliquots were removed from the heated sample using a pre-heated syringe (approximately 50° C), and introduced into the pre-heated FT-IR liquid cell (approximately 42° C). Six aliquots were taken from the same sealed 10-ml vial to make six replicate analyses to establish repeatability. Each analysis involved lowering the sample to the desired test temperature, and obtaining a spectrum at the desired test temperature. The Model Oil was analyzed at 18, 14.5, 5.1, and 0° C. to match the literature reference data points for direct comparison.

TABLE C

Model Oil Composition

| component | wt % |
|---|---|
| n-C$_{10}$ | 64.73 |
| n-C$_{20}$ | 10.30 |
| n-C$_{21}$ | 7.40 |
| n-C$_{22}$ | 5.29 |
| n-C$_{23}$ | 3.79 |
| n-C$_{24}$ | 2.70 |
| n-C$_{25}$ | 1.93 |
| n-C$_{26}$ | 1.37 |
| n-C$_{27}$ | 0.97 |
| n-C$_{28}$ | 0.69 |
| n-C$_{29}$ | 0.49 |
| n-C$_{30}$ | 0.35 |
| total | 100.00 |

Figure 5:
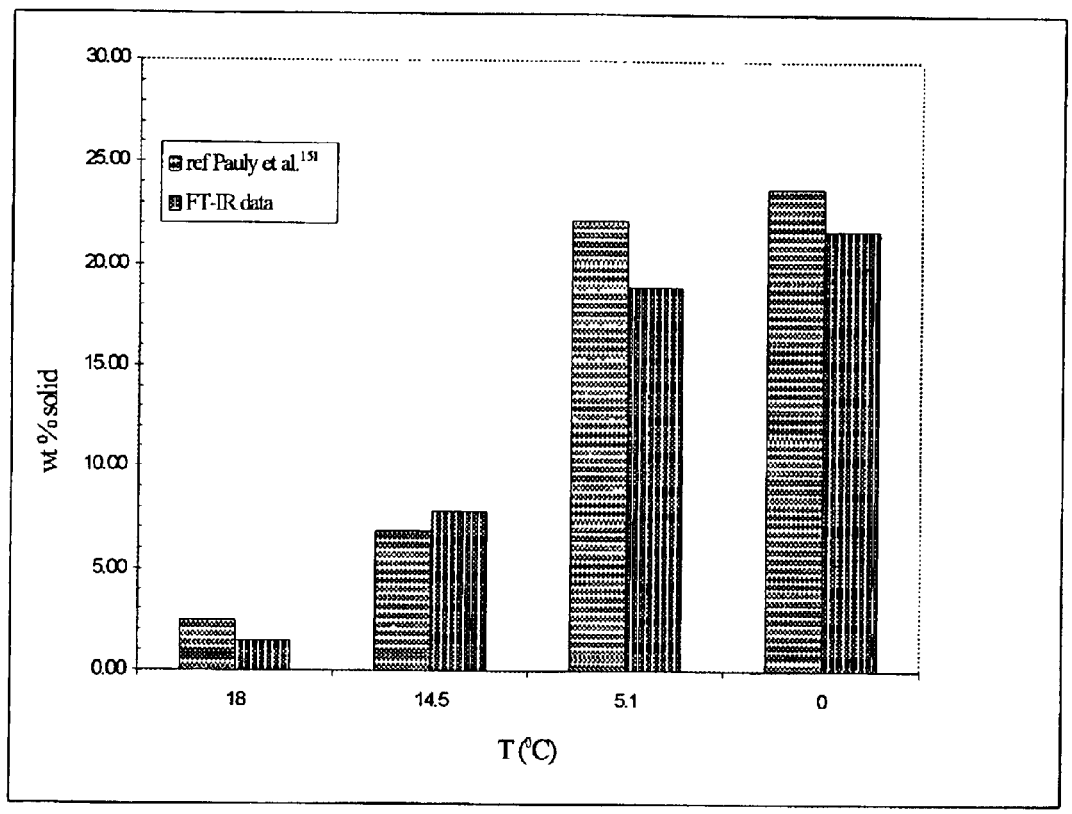
FIG. 5 is a bar graph showing data for wt % Solid versus Temperature from averaged data according to the FT-IR method according to the invention and reference data for Model Oil.

The spectra at 720 cm$^{-1}$ obtained for Model Oil Aliquot A at test temperatures are presented in FIG. 1. A doublet results at the lower temperatures, indicating the presence of orthorhombic crystals. A plot of peak area for the spectra in FIG. 1, obtained by integration from 735–715 cm$^{-1}$, versus temperature, is presented in FIG. 3. The WPT of 20° C. (±1.0° C.) indicated in FIG. 1 matches the 20.35° C. value for Mixture A in analysis of this oil by previous methods. A summary of the Model Oil wax precipitation data obtained is provided in Table D. The average WPT observed for the aliquots tested was 20° C, with a calculated relative standard deviation of 3.92%. It also should be noted that all but the highest temperature (where the solids content is lowest) show repeatability within 10% relative standard deviation (RSD) for weight percent solid. FIG. 5 provides a bar chart comparison of the averaged weight percent solids determined by FT-IR with the weight percent precipitated solids reported in Pauly, J.; Dauphin, C.; Daridon, J. Liquid-Solid Equilibria in a Decane+Multi-Paraffins System. *Fluid Phase Equilib.* 1998, 149, 191–207 As shown, the FT-IR data compare well with the literature reference data.

COMPARATIVE EXAMPLES

Conventional Wax Precipitation Temperature Measurements

Viscometry

The change in crude oil viscosity with temperature was used to indicate the WPT. However, unlike previous researchers who used rotational viscometers, the viscosities were determined using a capillary viscometer to minimize evaporative loss of crude oil light ends during analysis. The viscometry measurements were made by WTCI, in Houston, Tex. The capillary used was a coiled stainless steel tube, 305 cm long, with an internal radius of 0.054 cm. The test

TABLE D

Model Oil Wax Precipitation Data.

| Aliquot: | A | B | C | D | E | F | av | SD | RSD (%) |
|---|---|---|---|---|---|---|---|---|---|
| Reference[a] WPT (° C.) | | | Measured WPT (° C.) | | | | | | |
| 20.35 | 20 | 20 | 19 | 20 | 18 | 20 | 20 | 0.76 | 3.92 |

| T (° C.) | Reference[a] wt % Solid | Estimated wt % Solid Based on Peak (735–715 cm−1) Area | | | | | | | |
|---|---|---|---|---|---|---|---|---|---|
| 18.0 | 2.46 | 1.95 | 3.25 | −0.07 | | −0.18 | 2.57 | 1.50 | 1.56 | 103.51 |
| 14.5 | 6.80 | 6.81 | 8.85 | 7.32 | 7.96 | 7.65 | 8.48 | 7.84 | 0.75 | 9.59 |
| 5.1 | 22.16 | 16.74 | 19.36 | 19.10 | 18.89 | 19.61 | 20.28 | 19.00 | 1.20 | 6.34 |
| 0.0 | 23.71 | 18.88 | 22.38 | | 21.50 | 22.38 | 23.33 | 21.69 | 1.70 | 7.83 |

[a]ref Pauly et al.

Crude Oil Analysis

The ANS crude oil was sampled using a technique intended to prevent light end loss during sample heating to dissolve wax crystals. An aliquot of approximately 25 ml was taken from a well mixed 1 gallon can sample of ANS crude oil at room temperature (approximately 20° C.) and placed in a wide mouth jar with a Teflon coated lid. A room temperature syringe was then used to transfer the sample from the jar into the FT-IR liquid cell. The temperature of the FT-IR cell was then raised to 50° C. and held for one hour to dissolve any solids present, after which the sample was lowered to the test temperature for collection of FT-IR spectra. Set point temperatures were manually entered into the Brookfield HT-105 controller, which controlled the Brookfield TC-500 bath to produce coolant temperatures leaving the HC-32 liquid cell assembly within 0.1° C. of the desired set point. The sample temperature was monitored using the HH-22 digital thermometer, and manually recorded for each spectra obtained. In general, the sample cooling rates were always less than 0.2° C. per minute, and for the majority of testing the cooling rate was less than 0.1° C. per minute. These cooling rates produced minimal change in WPT values obtained using CPM as reported in Ronningsen, H. P.; Bjorndal, B.; Hansen, A. B.; Pedersen, W. B. Wax Precipitation from North Sea Oils. Crystallization and Dissolution Temperatures, and Newtonian and Non-Newtonian Flow Properties. *Energy Fuels* 1991, 5, 895–908. Several minutes were spent at a constant temperature prior to collection of spectra to insure equilibrium conditions.

method involved the determination of the pressure differential across the coiled tube under conditions of steady-state flow and constant temperature. The apparent dynamic viscosity was calculated using the Hagen-Poiseuille equation. A series of five shear rates (in terms of maximum shear rate calculated at the capillary tube wall) were used for each test temperature to identify any non-Newtonian behavior. The shear rates used ranged from 100 to 1000 sec$^{-1}$. Changing the speed of the injection pump produced the variation in shear rate.

The temperature and shear histories of the crude oil tested were carefully controlled by heating the sample in a closed liquid filled container to 65° C. for one hour to eliminate any solid structures present. The samples were then transferred to a piston accumulator maintained at 46° C., which fed the positive displacement injection pump used to provide system flow. Heating or cooling of the sample to test temperature was accomplished using coiled tubing placed in two individual temperature controlled water baths directly preceding the viscometer loop test section. Maintenance of the sample at test temperature was provided by placement of the capillary viscometer coil in a third temperature controlled water bath.

Thermocouples used to monitor the sample temperature were checked at the beginning and end of each testing day using a digital thermometer certified to ±0.3° C. from 40° C. to 100° C. using NIST traceable standards. The differential pressure across the capillary viscometer test section was measured with digital pressure transducers calibrated at the beginning and end of each testing day using a dead weight tester for five pressures ranging from 6.9 kPa to 2068.5 kPa.

Acceptable calibration values used for comparison between the thermocouple readout and the digital thermometer and between the differential pressure response and the dead weight tester were ±1.0° C., and ±0.5% of full scale respectively.

These limits were also used for indication of steady state conditions. Data were collected at 15 second intervals using laboratory data acquisition software, and experimental values for measured differential pressure were obtained by averaging of 15 data points collected sequentially during steady state operation. Precision attributed to measurement of viscosity by this procedure was demonstrated to be within 3.5% RSD, based on four tests using an oil standard (Fisher mineral oil).

Average viscosity values at the three highest temperatures were used to obtain the Arrhenius constants A and $E_a$, in equation 13 for dynamic viscosity ($\mu$). This was done by determining the slope and intercept from regression analysis with the linearized form of equation 13 given in equation 14.

$$\mu = (A)\exp(E_a/RT) \quad (13)$$

$$\ln \mu = \ln A + (E_a/RT) \quad (14)$$

A plot of the measured viscosity data and the viscosity calculated by the Arrhenius relation versus temperature allowed graphical determination of the point where an apparent change in the activation energy of flow ($E_a$) occurs. This change in the activation energy of flow as described in Eyring, H. Viscosity, Plasticity, and Diffusion as Examples of Absolute Reaction Rates. *J. Chem. Phys.* 1936, 4, 283–291, and was interpreted as the presence of solid wax particles in the crude oil sample. A plot of the experimental viscosity curves obtained for different shear rates in terms of log scale viscosity versus temperature also provided visual confirmation of non-Newtonian (shear-thinning) behavior at lower temperatures due to the presence of solids in the oil.

Cross-Polarized Microscopy

Cross-polarized microscopy (CPM) is the current preferred method used for identification of crude oil WPT. It involves viewing an oil sample under polarized light, where only light rotated by any crystalline material present would be visible. Under polarized light only solid wax crystals are observable with the exception of contaminants such as rust, silicates, solid salts, and water. Sample analysis is begun at 60° C., where any light visible is due to contaminants (well above observed wax dissolution temperatures for crude oil systems) to identify the presence of any contaminants present in the sample. As the sample temperature is reduced, the first appearance of solid crystals is taken to be the WPT.

Samples were prepared by filling micro-capillary cells (typical diameter less than 0.03 mm) with oil. The cell was glued to a glass slide with a micro-thermocouple for measurement of sample temperature. The sample slides were initially viewed at room temperature for wax crystals (quick indication of approximate WPT—above or below room temperature) and any obvious contaminants that could preclude analysis without initial processing of the sample for removal of water and particulates. The samples were heated on the microscope to 60° C. using a temperature controlled Peltier thermoelectric device. After 15 minutes for thermal equilibration at 60° C., an approximation of the WPT was obtained by lowering the sample temperature with a Peltier thermoelectric device in 5° C. increments. Several minutes at each temperature were sufficient to establish thermal equilibrium, at which time wax crystals were clearly identifiable as points of light. The sample was then reheated to 60° C. and held for 15 minutes to eliminate any crystals present. The sample was then cooled to the last temperature where no crystals had been observed during the initial WPT determination and held for 15 minutes to verify no crystals were present. The WPT of the sample was then determined by lowering the sample temperature in 1° C. increments until crystals were observed. The sample was held for 15 minutes at each test temperature. Temperature reduction was continued to 1° C. below the observed WPT to verify additional wax was precipitating. This process was repeated for each sample tested.

A Nikon Optophot-PDL microscope with total magnification of 100 X was used to perform this test, which allowed identification of crystals down to 1 micron in size. A series of five micro-capillary cells filled with the sample ANS crude oil were tested as duplicates. A standard deviation of 0.4° C. was calculated for these five duplicates, within the stated temperature measurement accuracy attributed to the thermocouple (±1.0° C.). CPM analyses were conducted at WTCI, in Houston, Tex.

Differential Scanning Calorimetry

Differential scanning calorimetry (DSC) thermograms for crude oil solids were generated using a procedure equivalent to ASTM D 4419–90. The method determined the melting onset temperature, the solid-liquid transition peak temperature, and the heat of fusion for the solids tested. The data were acquired, stored, and analyzed using computer software.

All DSC data were collected using a Dupont Instruments Thermal Analyst 2000 System, coupled with a Dupont Instruments 910 Differential Scanning Calorimeter. A T/A Instruments Liquid Nitrogen Cooling Assembly (LNCA) was used to cool the sample below ambient temperature between runs to insure a stable baseline for proper identification of the onset melting temperature. Hermetic sample pans were used to contain the sample, to prevent contamination of the DSC by boil over of melted wax. The samples were scanned at 10° C. per minute. Samples were initially heated to the final test temperature to melt the sample and obtain an even distribution of the sample on the bottom of the sample pan. The samples were then cooled below ambient for the actual data collection. Sample weights were between 5 and 10 mg, and were determined to ±0.0001 g using a Mettler AT250 balance. Prior to running the samples, an LCS of pure indium metal was run to insure proper instrument calibration and operation. Data analysis was performed using the Dupont Instruments DSC Standard Data Analysis Program.

The TIA Instruments LNCA was used to obtain test temperatures below the anticipated glass transition temperature of the crude oil tested (approximately −100° C.), in order to allow for baseline interpretation, and integration for total latent heat effects. The test methodology described in Hansen, A.; Pedersen, W.; Larsen, E.; Nielsen, A.; Ronningsen, H. Wax Precipitation from North Sea Oils. 3. Precipitation and Dissolution of Wax Studied by Differential Scanning Calorimety. *Energy Fuels* 1991, 5, 914–923 was employed. Problems believed to be related to the lack of stable baselines produced by the calorimeter in a cooling mode, and the low wax content of the ANS crude oil, precluded identification of an initial exotherm (indicating the WPT) on the DSC thermograms produced for the ANS crude oil tested.

DSC analysis of waxy crude oils did show distinct endotherms using sample cooling rates of 100 per minute for 5 to 10 mg samples contained in hermetically sealed sample pans. WPT values obtained from DSC analysis of waxy crude oils were used for comparison with WPT values obtained by CP Microscopy and FT-IR (see below). The DSC was calibrated according to manufacturer recommendations using an Indium standard (156.6° C. mp) supplied by Dupont Instruments, and a 99% pure n-$C_{12}$ standard (−12.0° C. mp) from Supelco. The calibrated DSC measured the onset melting temperature, as defined by ASTM D 4419–90 to be within ±1.0° C. of the literature melting points for the Indium and n-C12 standards.

Conventional Estimation of Weight Percent Solid Versus Temperature by Centrifuge A quantitative estimation of crude oil solid wax content at temperatures below the crude oil WPT was obtained by centrifugation of the samples. The presence of occluded oil in the solid samples produced precluded an exact determination of the precipitated solid wax content. The weight percent solid calculated for centrifuge testing of ANS crude oil samples were corrected for occluded oil using HTGC analysis of the solid samples produced from centrifugation.

Centrifuge Equipment

A Beckman Instruments Model J-6M induction drive centrifuge operating at 1500 rpm with a temperature controlled centrifuge chamber was used to centrifuge the crude oil samples. The centrifuge speed was calibrated and cross checked during testing using independent measurements from a precision tachometer mounted on the drive spindle and from a laser measuring device providing updated average values for centrifuge chamber rotation. Kimax 50-ml centrifuge tubes were used to hold the crude oil. Capping the tubes prevented loss of light ends during testing. Centrifugation of the samples at 1500 rpm produced an approximate gravity force of 450 g. The temperature of the centrifuge chamber was recorded with a digital thermometer certified to ±0.3° C. from −40° C. to 100° C. using NIST traceable standards. Centrifuge testing was conducted at WTCI, in Houston, Tex.

Centrifuge Procedure

Samples for centrifuge testing were prepared by placing 250 ml of oil contained in a glass bottle with a pressure seal cap previously aliquoted from the parent sample. The oil was heated to 65° C. and held at that temperature for 1 hour and then cooled to 38° C for transfer into eight duplicate 50-ml centrifuge tubes. The filled centrifuge tubes were weighed and placed in a temperature controlled water bath, which was monitored by the calibrated centrifuge digital thermometer. The tubes were cooled to the centrifuge test temperatures (21, −1, −18° C.) at a controlled rate while the centrifuge was equilibrated at the same test temperature. Once samples and centrifuge were at test temperature, the centrifuge tubes were placed in the centrifuge and spun for a minimum of 40 hours at 1500 rpm. The liquid phase was decanted and each tube was swabbed to remove residual liquid. The tubes were re-weighed to obtain solid content by difference.

Results and Discussion

Experimental values for WPT for the ANS crude oil tested are summarized in Table E. No values are proved for provided for DSC measurement as it was not possible to identify a distinct exotherm due to the changing baseline of the calorimeter used for analysis. The values for WPT by CPM and FT-IR match within stated precision estimates despite the measurements being made on samples of ANS crude oil taken from different sample cans. This possible variable could not be eliminated due to the different laboratory locations (CPM, viscometry at WTCI in Houston, Tex., and FT-IR in Salt Lake City, Utah). Variation in the ANS samples, while unknown, would not be expected to introduce compositional difference adequate to affect WPT measured values using the sample handling procedures discussed previously.

TABLE E

Summary of ANS Crude Oil WPT Measurements

| | WPT (° C.) | | |
|---|---|---|---|
| CP microscopy | FT-IR | DSC | viscometry |
| 25 | 25 | no data | 19 |

The value for WPT obtained by viscometry is 6° C. lower than the value obtained by CPM. This difference is slightly larger than typical results in other comparative studies, however, it is observed by CPM and videomicroscopy that the wax formed in ANS crude oil is comprised of rounded (1–2 micron) crystals in comparison with large platelet and needle shaped crystals present in more waxy oils. Because of these rounded crystals, the ANS crude oil would be expected to require a higher solids content to affect sample viscosity.

Figure 6:
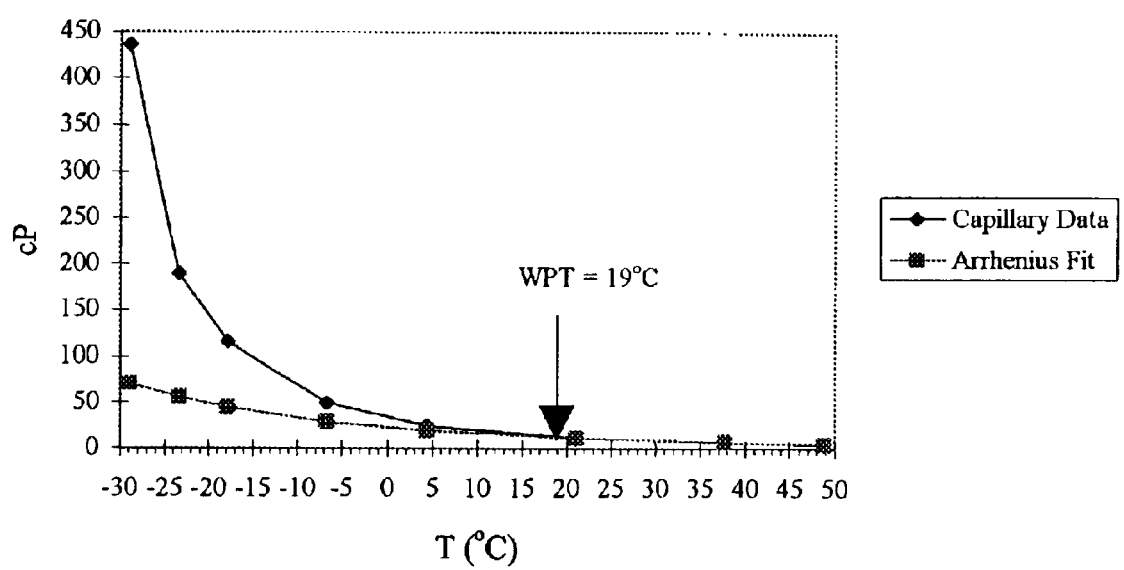
FIG. 6 is a graph showing ANS crude oil viscosity versus temperature.
Figure 7:
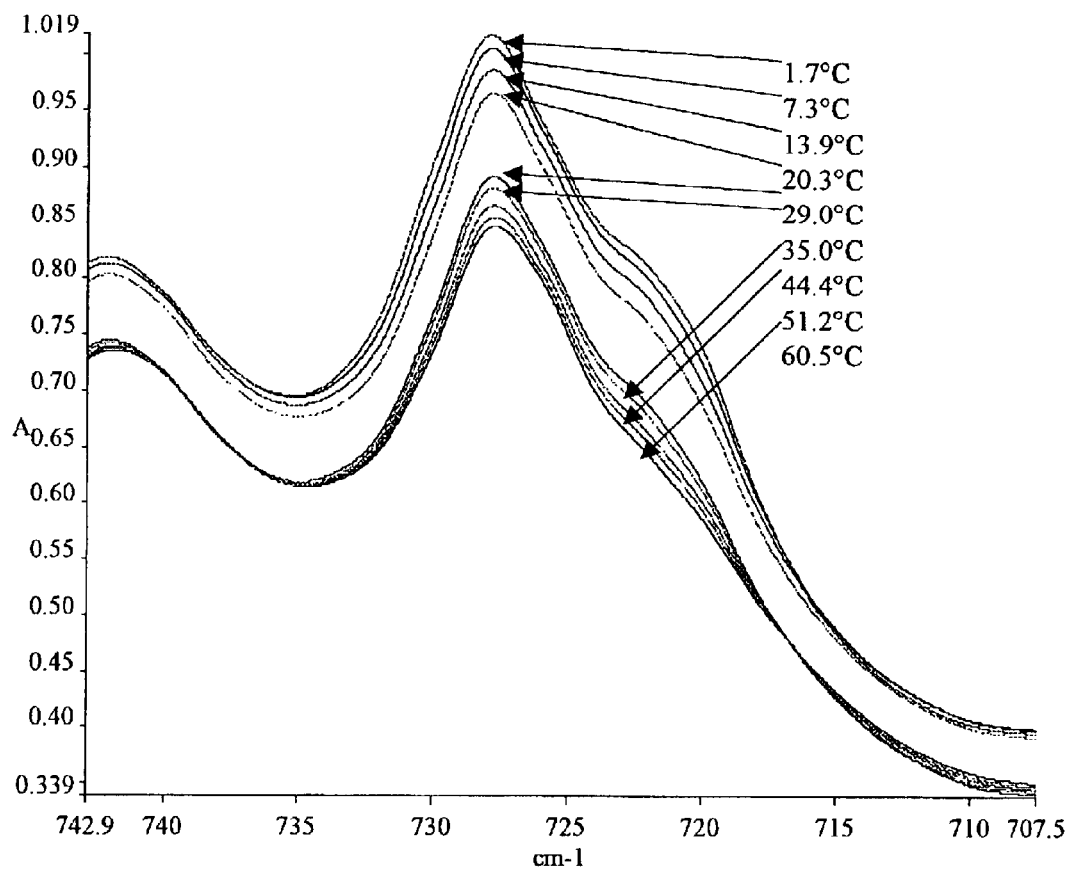
FIG. 7 is a graph showing FT-IR spectra of ANS crude oil.
Figure 8:
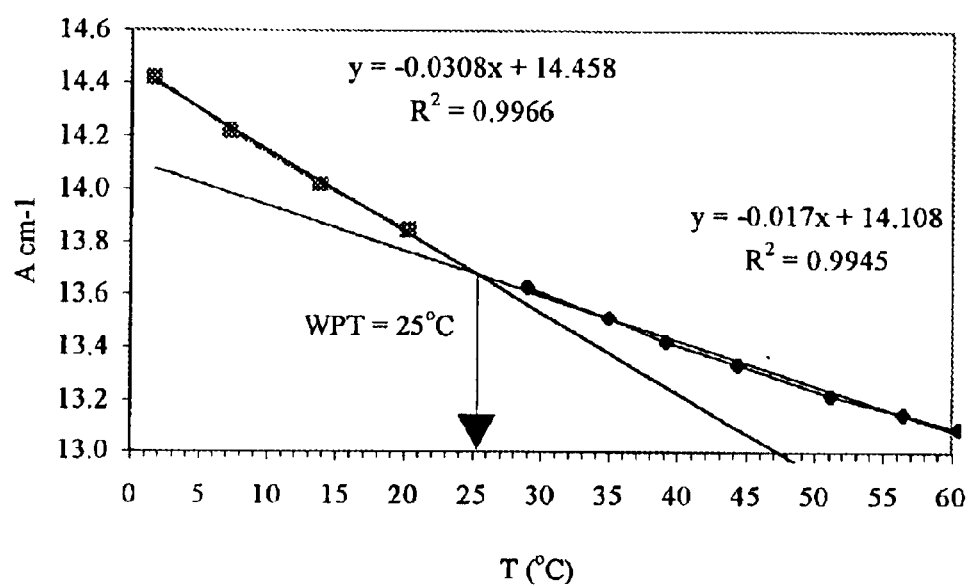
FIG. 8 is a graph showing Peak Area (735–715 cm$^{-1}$) versus Temperature of ANS Crude Oil.

The plot of viscosity versus temperature used to identify the WPT for ANS crude oil by viscometry is given in FIG. 6. The FT-IR spectra obtained for the ANS crude oil are provided in FIG. 7. It is important to note that the increased absorbance of the 720 $cm^{-1}$ band attributed to rocking of long chain methylene groups only produces an enlarged shoulder on the peak without splitting into a doublet over the range of temperatures tested. This could indicate reduced crystallinity of the solid formed. The plot of FT-IR absorbance (in terms of peak area from 735 to 715 $cm^{-1}$) versus temperature used to identify the WPT for ANS crude oil is shown in FIG. 8.

Weight Percent Solid Wax Versus Temperature

Results for experimental estimation of solid wax content associated with decreasing crude oil sample temperature using centrifuge testing and FT-IR analysis were found to be complimentary. The data for ANS crude oil was obtained as described above and is shown in FIG. 9

Figure 9:
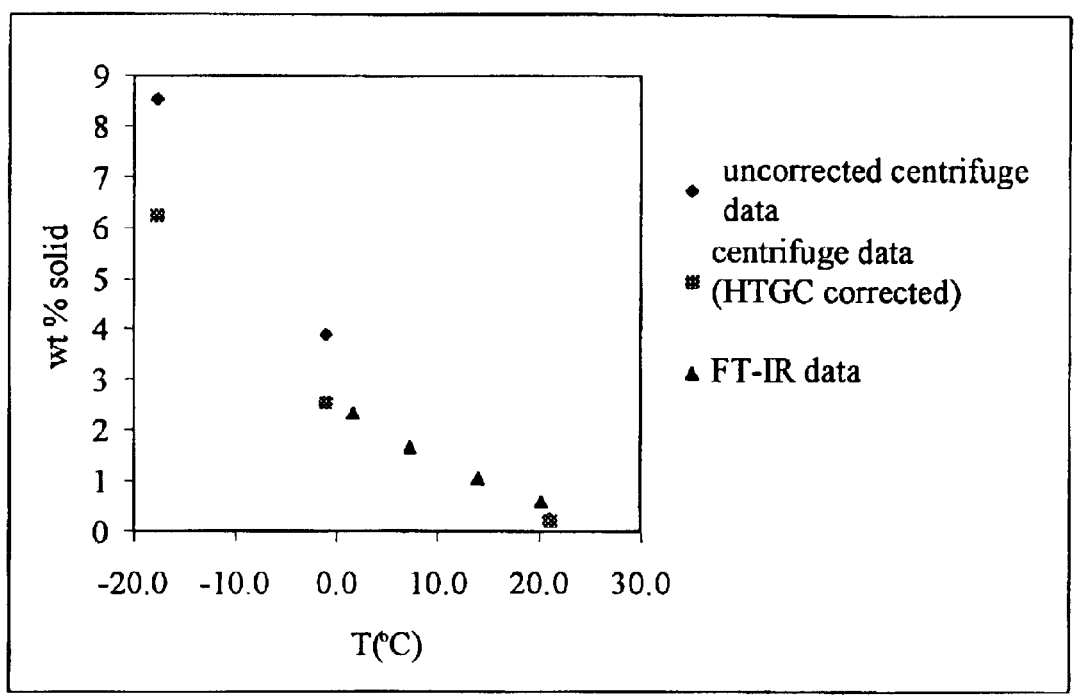
FIG. 9 is a graph showing Weight Percent Solid versus Temperature data by the FT-IR method of the invention and by Centrifuge.

The centrifuge data, which has been corrected by HTGC for occluded oil, brackets the FT-IR data as shown in FIG. 9. The ANS crude oil was found to precipitate 0.2, 2.6, and 6.2 wt % solid wax at 21,−1, and −18° C. respectively.

FT-IR Data for Crude Oils from the Gulf of Mexico and Grand County Utah

Figure 10:
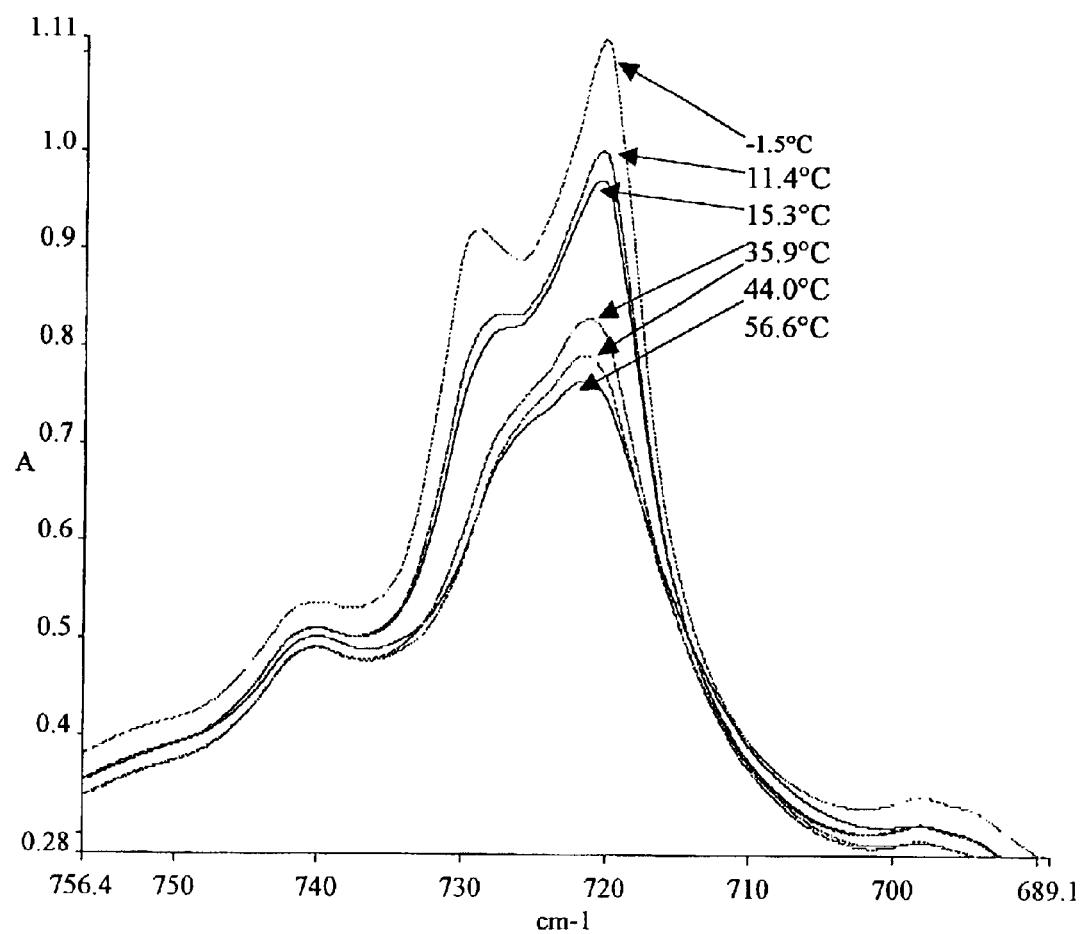
FIG. 10 is a graph showing FT-IR spectra at 720 cm$^{-1}$ for Utah-Grand County crude oil.
Figure 11:
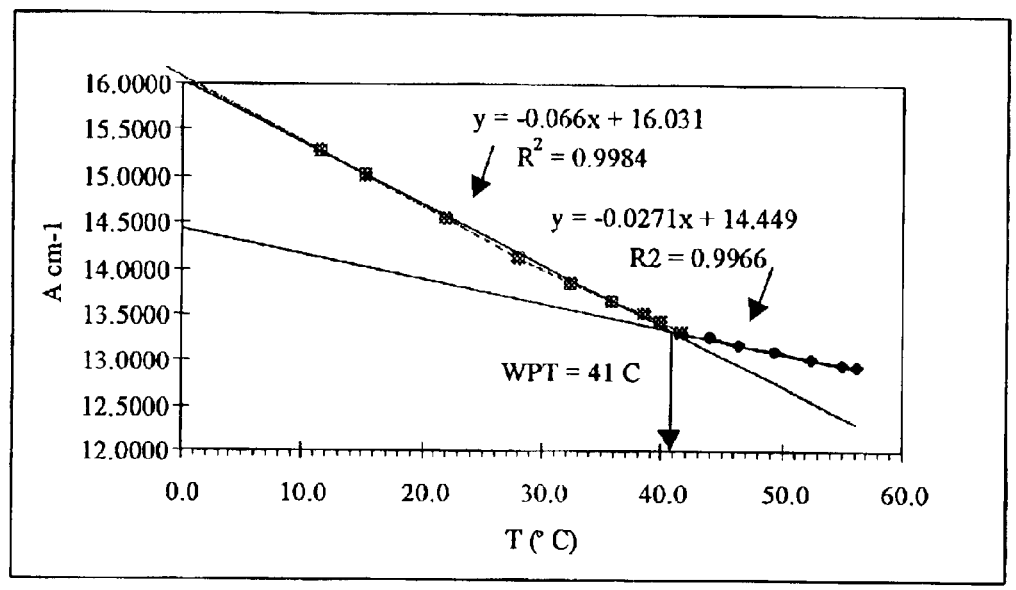
FIG. 11 is a graph showing Peak Area (735–715 cm$^{-1}$) versus Temperature for Utah-Grand County crude oil.
Figure 12:
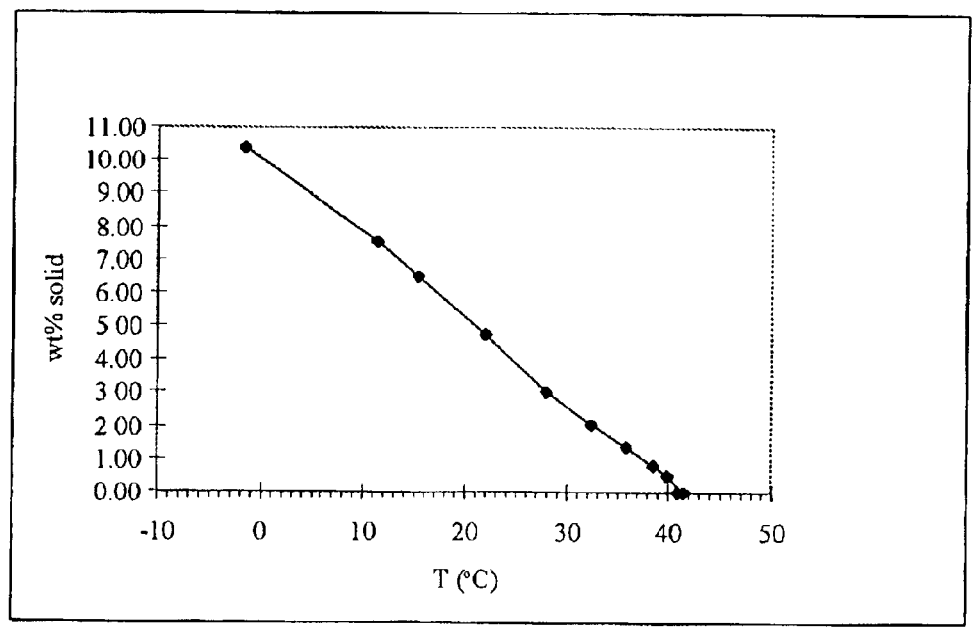
FIG. 12 is a graph showing Weight Percent Solid versus Temperature data by the FT-IR method of the invention for Utah-Grand County crude oil.

Additional FT-IR analyses were conducted on several crude oils other than ANS, to demonstrate the applicability of the FT-IR method. The crude oils tested included waxy oils from the Gulf of Mexico and Grand County, Utah. WPT values were measured using FT-IR (essentially as described above) for Gulf of Mexico (proprietary source), and Utah-Grand County crude oils. The results are compared in Table F with other WPT data generated for these oils. These oils are considered to be waxy crude oils. No aromatic carbon was found in the Utah-Grand County crude oil by $^{13}C$ NMR analysis. The high paraffinicity of the Utah-Grand County crude oil is also demonstrated in FIG. 10, where it is observed that a doublet develops in the spectra around 720.7 $cm^{-1}$ at the lowest test temperatures indicating the presence of orthorhombic crystals. The identification of the WPT for the Utah-Grand County crude oil is shown in FIG. 11. The weight percent precipitated solids versus temperature as estimated by FT-IR analysis for the Utah-Grand County Oil is given in FIG. 12.

Figure 13:
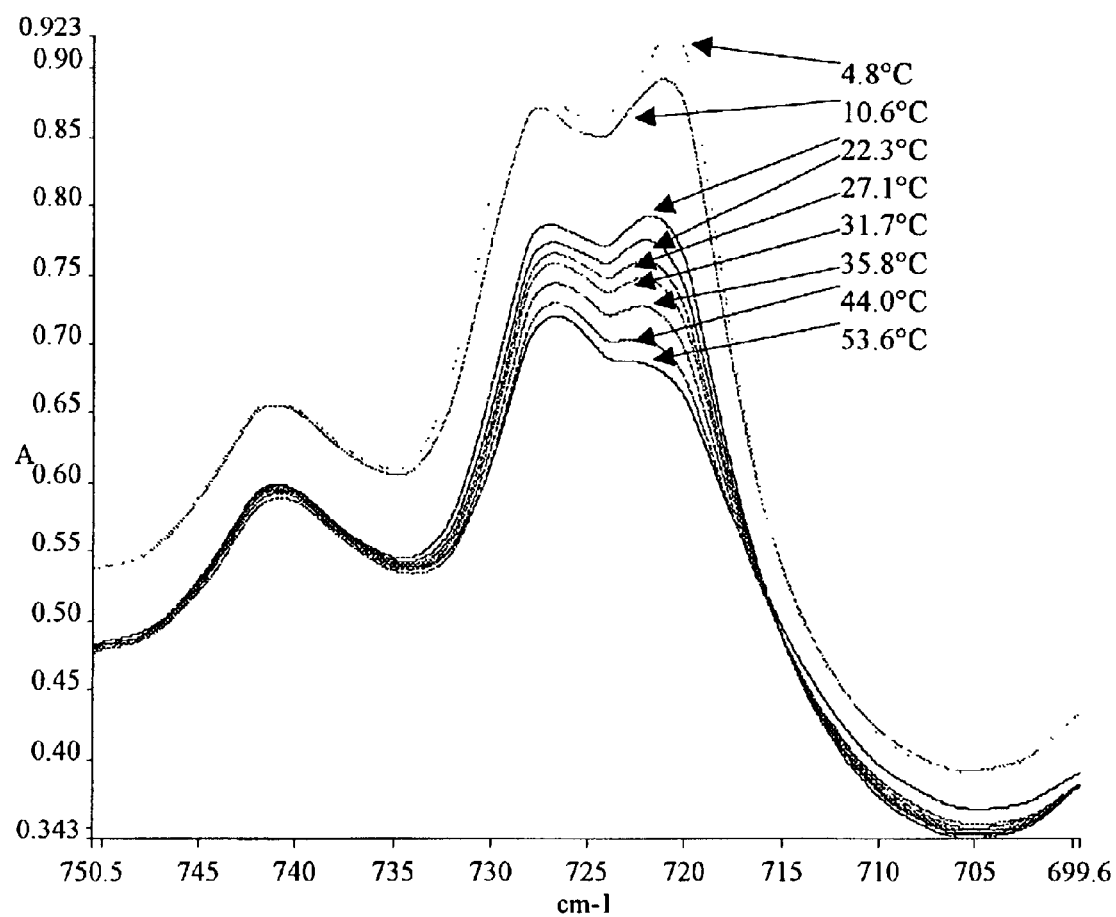
FIG. 13 is a graph showing FT-IR spectra at 720 cm$^{-1}$ for Gulf of Mexico Crude Oil.
Figure 14:
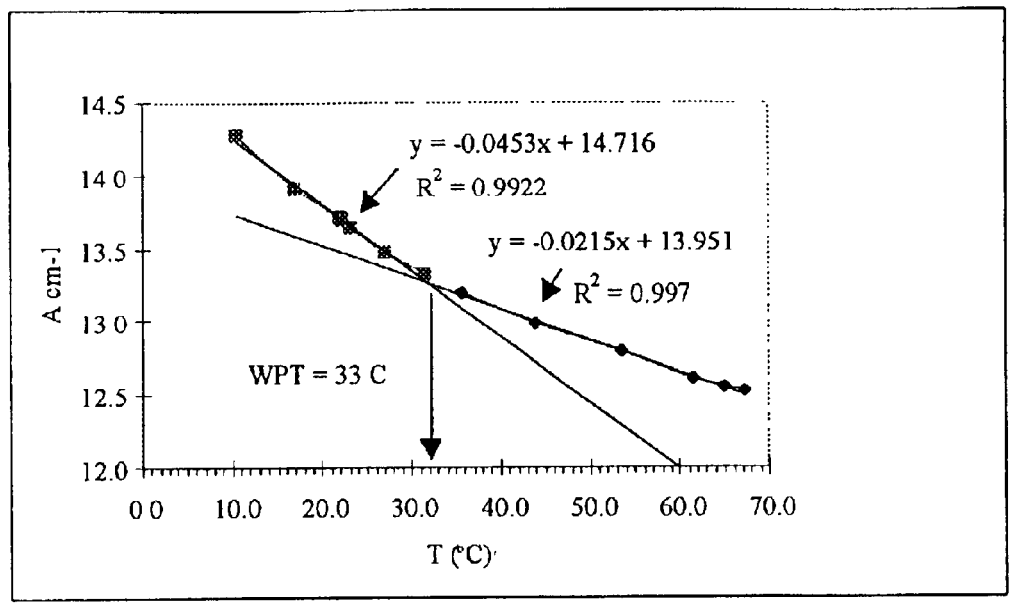
FIG. 14 is a graph showing Peak Area (735–715 cm$^{-1}$) versus Temperature for Gulf of Mexico Crude Oil.
Figure 15:
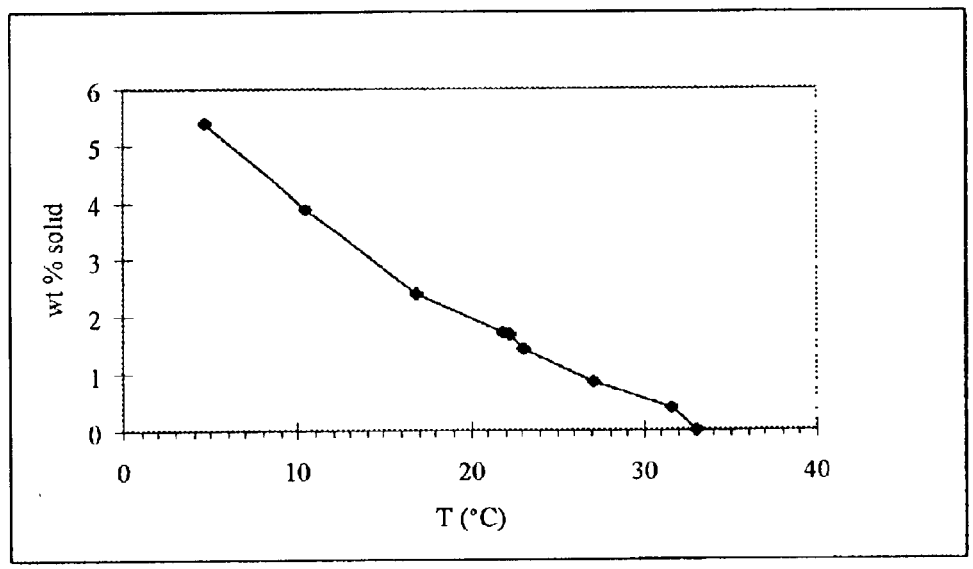
FIG. 15 is a graph showing Weight Percent Solid versus Temperature data by the FT-IR method of the invention for Utah-Grand County crude oil.

The spectra at 720 $cm^{-1}$ obtained for the Gulf of Mexico crude oil at various test temperatures is given in FIG. 13. The graphical indication of the WPT for the Gulf of Mexico crude oil is shown in FIG. 14. The weight percent precipitated solids versus temperature as estimated by FT-IR analysis for the Gulf of Mexico oil is given in FIG. 15. It is observed that the estimated 1 to 2 wt % solids content corresponds well with the observed gelling of the oil around room temperature (a solid content of 2 wt % has been observed to induce gel behavior in this crude oil).

TABLE F

Waxy Crude Oil-Wax Precipitation Temperature Measurements Summary.

| crude oil | WPT (° C.) | | | |
|---|---|---|---|---|
| | CP Microscopy | FT-IR | DSC | Viscometry |
| Utah-Grand County | no data | 41 | 34 | no data |
| Gulf of Mexico | 34 | 33 | 27 | no data |

A description of experimental work relating to the present invention is found in Roehner, Richard Mark, *Measurement and prediction of wax precipitation for Alaskan North Trans-Alaska Pipeline System*, Dissertation submitted to the faculty of The University of Utah, Department of Chemical and Fuels Engineering, August, 2000, which is hereby incorporated by reference.

While this invention has been described with reference to certain specific embodiments and examples, it will be recognized by those skilled in the art that many variations are possible without departing from the scope and spirit of this invention, and that the invention, as described by the claims, is intended to cover all changes and modifications of the invention which do not depart from the spirit of the invention.

What is claimed is:

1. A method of determining wax precipitation temperature (WPT) for a liquid hydrocarbon sample, the method comprising:

Measuring infra-red light absorbance of the sample,

The measuring made at a plurality of temperatures at a same wave number to obtain a plurality of data points of total absorbance ($A_{TOTAL}$) vs. temperature (T), the wave number corresponding to a wavelength at which the infrared light is absorbed by long chain methylene on a molecule, calculating by a linear regression a slope ($S_S$) of $A_{TOTAL}$ vs. T from the data points in which a solid phase is apparent and are data points below the WPT, calculating by a linear regression a slope ($S_L$) of $A_{TOTAL}$ vs. T from the data points in which the sample is essentially free of a solid phase and are data points above the WPT, calculating the temperature which is at the intersection of lines $A_{TOTAL}=T*S_S$ and $A_{TOTAL}=T*S_L$, which temperature is the determined wax precipitation temperature.

2. A method of determining wax precipitation temperature (WPT) and percent solid for a liquid hydrocarbon sample, the method comprising:

measuring infrared light absorbance of the sample, the measuring made at a plurality of temperatures at a same wave number to obtain a plurality of data points of total absorbance ($A_{TOTAL}$) vs. temperature (T), the wave number corresponding to a wavelength at which the infrared light is absorbed by long chain methylene on a molecule, calculating by a linear regression a slope ($S_S$) of $A_{TOTAL}$ vs. T from the data points in which a solid phase is apparent, calculating by a linear regression a slope ($S_L$) of $A_{TOTAL}$ vs. T from the data points in which the sample is essentially free of a solid phase, calculating the temperature which is at the intersection of lines $A_{TOTAL}=T*S_S$ and $A_{TOTAL}=T*S_L$, which temperature is the determined wax precipitation temperature;

calculating the weight percent of solids of the liquid hydrocarbon sample at a selected temperature ($T_S$) below the WPT from the data points of $A_{TOTAL}$ vs. T by the equation;

$$\text{wt. \% } S = [(A_{TOTAL} - A_L)/A_{TOTAL}] \times 100$$

where wt. % S is the weight percent of solids, where $A_L$ is the liquid absorbance at the selected temperature determined by linear extrapolation of the line $A_{TOTAL}=T*S_L$, derived from data points in the liquid phase of total absorbance vs. temperature to the selected temperature below the WPT, such that $A_L$ is derived from the equation;

$$A_L = T_S * S_L.$$

3. A method as in claim 1 wherein the petroleum sample is crude oil.

4. A method for determining solid/liquid properties of a petroleum sample, the method comprising;

measuring integrated absorbance of the sample at a wave number near 720 cm$^{-1}$ that corresponds to the CH$_2$ rocking vibration of long chain methylene (LCM), the measuring made at a plurality of temperatures at the same wave number to obtain a plurality of data points of total absorbance ($A_{TOTAL}$) vs. temperature, determining the wax precipitation temperature (WPT) from the data points by calculating the temperature at which the linear slope of total absorbance vs. temperature changes as the data points change from the those below the WPT to those above the WPT.

5. A method as in claim 4 additionally comprising;

determining the weight percent of solids (wt. % S) of the petroleum sample at a selected temperature below the WPT from the $A_{TOTAL}$ at the selected temperature by the equation:

$$\text{wt. \% } S = [(A_{TOTAL} - A_L)/A_{TOTAL}] \times 100$$

where $A_L$ is the liquid absorbance at the selected temperature determined by extrapolating the data of total absorbance vs. temperature from the data points above the WPT to the selected temperature below the WPT.

6. An apparatus for determining wax precipitation temperature and percent solids for a liquid hydrocarbon sample, the apparatus comprising:

an absorbance detector for measuring the infra-red light absorbance of the sample, the measuring made at a plurality of temperatures at a same wave number to obtain a plurality of data points of total absorbance ($A_{TOTAL}$) vs. temperature (T), the wave number corresponding to a wavelength at which the infrared light is absorbed by long chain methylene on a molecule;

a calculator for calculating by a linear regression a slope ($S_S$) of $A_{TOTAL}$ vs. T from the data points in which a solid phase is apparent, calculating by a linear regression a slope ($S_L$) of $A_{TOTAL}$ vs. T from the data points in which the sample is essentially free of a solid phase, calculating the temperature which is at the intersection of lines $A_{TOTAL}=T*S_S$ and $A_{TOTAL}=T*S_L$, which temperature is the determined wax precipitation temperature;

calculating the weight percent of solids of the liquid hydrocarbon sample at a selected temperature ($T_S$) below the WPT from the data points of $A_{TOTAL}$ vs. T by the equation;

$$\text{wt. \% } S=[(A_{TOTAL}-A_L)/A_{TOTAL}]\times 100$$

where wt. % S is the weight percent of solids, where $A_L$ is the liquid absorbance at the selected temperature determined by linear extrapolation of the line $A_{TOTAL}=T*S_L$, derived from data points in the liquid phase of total absorbance vs. temperature to the selected temperature below the WPT, such that $A_L$ is derived from the equation;

$$A_L=T_S*S_L.$$

7. An apparatus for determining solid/liquid properties of a petroleum sample, the apparatus comprising;

means for measuring integrated absorbance of the sample at a wave number near 720 cm$^{-1}$ that corresponds to the CH$_2$ rocking vibration of long chain methylene (LCM), the measuring made at a plurality of temperatures at the same wave number to obtain a plurality of data points of total absorbance ($A_{TOTAL}$) vs. temperature, means for determining the wax precipitation temperature (WPT) from the data points by calculating the temperature at which the linear slope of total absorbance vs. temperature changes as the data points change from the those below the WPT to those above the WPT.

8. An apparatus as in claim 7 additionally comprising;

means for determining the weight percent of solids (wt. % S) of the petroleum sample at a selected temperature below the WPT from the $A_{TOTAL}$ at the selected temperature by the equation:

$$\text{wt. \% } S=[(A_{TOTAL}-A_L)/A_{TOTAL}]\times 100$$

where $A_L$ is the liquid absorbance at the selected temperature determined by extrapolating the data of total absorbance vs. temperature from the data points above the WPT to the selected temperature below the WPT.

* * * * *